(12) United States Patent
Asahina et al.

(10) Patent No.: US 7,915,427 B2
(45) Date of Patent: Mar. 29, 2011

(54) PROCESS FOR PRODUCING AMINOACETYL PYRROLIDINE CARBONITRILE DERIVATIVE AND INTERMEDIATE FOR PRODUCTION THEREOF

(75) Inventors: Yoshikazu Asahina, Tochigi (JP); Yasumichi Fukuda, Tochigi (JP); Futoshi Shiga, Tochigi (JP)

(73) Assignee: Kyorin Pharmaceuticals Co., Ltd., Tokyo (JP)

( * ) Notice: Subject to any disclaimer, the term of this patent is extended or adjusted under 35 U.S.C. 154(b) by 278 days.

(21) Appl. No.: 12/224,849

(22) PCT Filed: Feb. 2, 2007

(86) PCT No.: PCT/JP2007/051768
§ 371 (c)(1),
(2), (4) Date: Sep. 8, 2008

(87) PCT Pub. No.: WO2007/102286
PCT Pub. Date: Sep. 13, 2007

(65) Prior Publication Data
US 2009/0048454 A1    Feb. 19, 2009

(30) Foreign Application Priority Data
Mar. 8, 2006   (JP) ................. 2006-062548

(51) Int. Cl.
C07D 207/04    (2006.01)
(52) U.S. Cl. ........................ 548/400; 548/578
(58) Field of Classification Search .......... 548/400, 548/578
See application file for complete search history.

(56) References Cited

U.S. PATENT DOCUMENTS

| | | | |
|---|---|---|---|
| 5,939,560 A | 8/1999 | Jenkins et al. | |
| 5,965,764 A | 10/1999 | Matsuoka et al. | |
| 6,166,063 A | 12/2000 | Villhauer | |
| 0,031,780 A1 | 10/2001 | Kanstrup et al. | |
| 6,303,661 B1 | 10/2001 | Demuth et al. | |
| 6,432,969 B1 | 8/2002 | Villhauer | |
| 0,193,390 A1 | 12/2002 | Villhauer | |
| 6,849,622 B2 | 2/2005 | Yasuda et al. | |
| 7,132,443 B2 | 11/2006 | Haffner et al. | |
| 7,138,397 B2 | 11/2006 | Yasuda et al. | |
| 7,160,877 B2 | 1/2007 | Yasuda et al. | |
| 7,183,290 B2 | 2/2007 | Haffner et al. | |
| 7,196,201 B2 | 3/2007 | Haffner et al. | |
| 7,268,150 B2 | 9/2007 | Hayakawa et al. | |
| 7,332,487 B2 | 2/2008 | Yasuda et al. | |
| 7,348,327 B2 | 3/2008 | Aranyi et al. | |
| 7,514,571 B2 | 4/2009 | Fukuda et al. | |
| 7,560,569 B2 | 7/2009 | Fukuda et al. | |
| 7,666,869 B2 | 2/2010 | Yasuda et al. | |
| 0,099,892 A1 | 4/2010 | Orita et al. | |
| 7,754,757 B2 | 7/2010 | Fukuda et al. | |
| 2001/0025023 A1 | 9/2001 | Carr | |
| 2002/0006899 A1 | 1/2002 | Pospisilik et al. | |
| 2002/0019339 A1 | 2/2002 | Naughton | |
| 2002/0019411 A1 | 2/2002 | Robl et al. | |
| 2002/0037829 A1 | 3/2002 | Aronson et al. | |
| 2002/0103384 A1 | 8/2002 | Kanstrup et al. | |
| 2002/0110560 A1 | 8/2002 | Demuth et al. | |
| 2003/0100563 A1 | 5/2003 | Edmondson et al. | |
| 2003/0105077 A1 | 6/2003 | Kanstrup et al. | |
| 2003/0176357 A1 | 9/2003 | Pospisilik et al. | |
| 2003/0225102 A1 | 12/2003 | Sankaranarayanan | |
| 2004/0017848 A1 | 1/2004 | Doan et al. | |
| 2004/0063935 A1 | 4/2004 | Yasuda et al. | |
| 2004/0072892 A1 | 4/2004 | Fukushima et al. | |
| 2004/0082607 A1 | 4/2004 | Oi et al. | |
| 2004/0106655 A1 | 6/2004 | Kitajima et al. | |
| 2004/0106802 A1 | 6/2004 | Sankaranarayanan | |
| 2004/0121964 A1 | 6/2004 | Madar et al. | |
| 2004/0152745 A1 | 8/2004 | Jackson et al. | |
| 2004/0167133 A1 | 8/2004 | Edmondson et al. | |

(Continued)

FOREIGN PATENT DOCUMENTS
JP        09-509921        10/1997
(Continued)

OTHER PUBLICATIONS

International Search Report issued May 1, 2007 in the International (PCT) Application PCT/JP2007/051768 of which the present application is the U.S. National Stage.

(Continued)

*Primary Examiner* — Rebecca L Anderson
*Assistant Examiner* — Samantha L Shterengarts
(74) *Attorney, Agent, or Firm* — Wenderoth, Lind & Ponack, L.L.P.

(57) ABSTRACT

Novel intermediates for the production of aminoacetyl pyrrolidine carbonitrile derivatives ensure the safe and efficient production of the compounds. Specifically, the present invention provides a sulfonyloxyacetyl pyrrolidine derivative, represented by the following formula:
(Chemical Formula 1)

Formula 1:

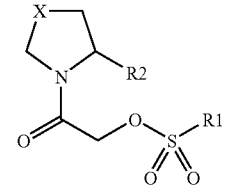

(wherein R1 is a substituted or unsubstituted $C_1$-$C_6$ alkyl group, a substituted or unsubstituted $C_3$-$C_6$ cycloalkyl group, a substituted or unsubstituted arylmethyl group, a substituted or unsubstituted aromatic hydrocarbon, a substituted or unsubstituted aromatic heterocyclic ring or a substituted or unsubstituted aliphatic heterocyclic ring; R2 is $CONH_2$ or CN; and X is $CH_2$, CHF or $CF_2$.)

9 Claims, No Drawings

U.S. PATENT DOCUMENTS

| | | |
|---|---|---|
| 2004/0167341 A1 | 8/2004 | Haffner et al. |
| 2004/0176428 A1 | 9/2004 | Edmondson et al. |
| 2004/0229926 A1 | 11/2004 | Yasuda et al. |
| 2004/0242636 A1 | 12/2004 | Haffner et al. |
| 2005/0054678 A1 | 3/2005 | Yasuda et al. |
| 2005/0070719 A1 | 3/2005 | Belyakov et al. |
| 2005/0107308 A1 | 5/2005 | Pospisilik et al. |
| 2005/0107309 A1 | 5/2005 | Demuth et al. |
| 2005/0130981 A1 | 6/2005 | Aranyl et al. |
| 2005/0148606 A1 | 7/2005 | Kanstrup et al. |
| 2005/0153973 A1 | 7/2005 | Aranyl et al. |
| 2005/0164989 A1 | 7/2005 | Abe et al. |
| 2005/0176771 A1 | 8/2005 | Hayakawa et al. |
| 2005/0245538 A1 | 11/2005 | Kitajima et al. |
| 2005/0266080 A1 | 12/2005 | Desai et al. |
| 2006/0142585 A1 | 6/2006 | Thomas et al. |
| 2006/0173056 A1 | 8/2006 | Kitajima et al. |
| 2006/0210627 A1 | 9/2006 | Pfeffer et al. |
| 2006/0241146 A1 | 10/2006 | Yasuda et al. |
| 2006/0270679 A1 | 11/2006 | Edmondson et al. |
| 2007/0112059 A1 | 5/2007 | Fukushima et al. |
| 2007/0112205 A1 | 5/2007 | Fukushima et al. |
| 2007/0167501 A1 | 7/2007 | Fukuda et al. |
| 2007/0265320 A1 | 11/2007 | Fukuda et al. |
| 2008/0038341 A1 | 2/2008 | Kowalski et al. |
| 2008/0050443 A1 | 2/2008 | Kowalski et al. |
| 2008/0146818 A1 | 6/2008 | Fukuda et al. |

FOREIGN PATENT DOCUMENTS

| | | |
|---|---|---|
| JP | 11-322701 | 11/1999 |
| JP | 2000-511559 | 9/2000 |
| JP | 2002-531547 | 9/2002 |
| JP | 2002-356471 | 12/2002 |
| JP | 2002-356472 | 12/2002 |
| JP | 2003-520849 | 7/2003 |
| JP | 03-531118 | 10/2003 |
| JP | 2003-535034 | 11/2003 |
| JP | 2004-2367 | 1/2004 |
| JP | 2004-2368 | 1/2004 |
| JP | 2004-26820 | 1/2004 |
| JP | 2004-503531 | 2/2004 |
| JP | 2005-500321 | 1/2005 |
| JP | 2005-529078 | 9/2005 |
| JP | 2005-532369 | 10/2005 |
| JP | 2006-160733 | 6/2006 |
| JP | 2007-518760 | 7/2007 |
| JP | 2008-501025 | 1/2008 |
| JP | 2008-510764 | 4/2008 |
| JP | 2008-527004 | 7/2008 |
| JP | 2008-239543 | 10/2008 |
| JP | 2008-290969 | 12/2008 |
| JP | 2008-543773 | 12/2008 |
| JP | 2009-114127 | 5/2009 |
| JP | 2010-70454 | 4/2010 |
| WO | 95/015309 | 6/1995 |
| WO | 97/040832 | 11/1997 |
| WO | 98/19998 | 5/1998 |
| WO | 2000/034241 | 6/2000 |
| WO | 01/034594 | 5/2001 |
| WO | 01/055105 | 8/2001 |
| WO | 01/062266 | 8/2001 |
| WO | 01/068603 | 9/2001 |
| WO | 01/96295 | 12/2001 |
| WO | 02/014271 | 2/2002 |
| WO | 02/030890 | 4/2002 |
| WO | 02/30891 | 4/2002 |
| WO | 02/38541 | 5/2002 |
| WO | 02/062764 | 8/2002 |
| WO | 03/000180 | 1/2003 |
| WO | 03/002530 | 1/2003 |
| WO | 03/002531 | 1/2003 |
| WO | 03/002553 | 1/2003 |
| WO | 03/004496 | 1/2003 |
| WO | 03/004498 | 1/2003 |
| WO | 03/015775 | 2/2003 |
| WO | 03/017936 | 3/2003 |
| WO | 03/057144 | 7/2003 |
| WO | 03/057666 | 7/2003 |
| WO | 03/002553 | 9/2003 |
| WO | 03/074500 | 9/2003 |
| WO | 03/080633 | 10/2003 |
| WO | 03/084940 | 10/2003 |
| WO | 03/095425 | 11/2003 |
| WO | 03/106456 | 12/2003 |
| WO | 2004/007446 | 1/2004 |
| WO | 2004/009544 | 1/2004 |
| WO | 2004/026822 | 4/2004 |
| WO | 2004/099185 | 11/2004 |
| WO | 2005/067976 | 7/2005 |
| WO | 2005/075421 | 8/2005 |
| WO | 2005/077900 | 8/2005 |
| WO | 2005/082847 | 9/2005 |
| WO | 2005/117841 | 12/2005 |
| WO | 2006/021455 | 3/2006 |
| WO | 2006/040625 | 4/2006 |
| WO | 2006/043595 | 4/2006 |
| WO | 2006/078593 | 7/2006 |
| WO | 2006/135723 | 12/2006 |
| WO | 2008/096841 | 8/2008 |
| WO | 2010/016584 | 2/2010 |
| WO | 2010/018866 | 2/2010 |
| WO | 2010/032723 | 3/2010 |

OTHER PUBLICATIONS

Edwin B. Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties", J. Med. Chem., 46, pp. 2774-2789, 2003.

Hiroshi Fukushima et al., "Synthesis and structure-activity relationships of potent 3- or 4-substituted-2-cyanopyrrolidine dipeptidyl peptidase IV inhibitors", Bioorganic & Medicinal Chemistry, 12, pp. 6053-6061, 2004.

International Search Report issued May 13, 2008 with Written Opinion in International (PCT) Application No. PCT/JP2008/055202 (with English translation).

International Search Report issued Mar. 15, 2005 with Written Opinion in International (PCT) Application No. PCT/JP2005/001377 (with English translation).

Japanese Office Action issued Jan. 9, 2007 in Japanese Application No. 2005-517671 (with English translation).

U.S. Office Action issued Apr. 3, 2009 in U.S. Appl. No. 10/588,660.

U.S. Office Action issued Oct. 20, 2008 in U.S. Appl. No. 10/588,660.

New Zealand Office Action issued Feb. 12, 2009 in New Zealand Patent Application No. 548440.

Australian Office Action issued Oct. 9, 2007 in Australian Application No. 2005210285.

Chinese Office Action issued Oct. 17, 2008 in Chinese Application No. 200580004191.8 (English Translation only).

Chinese Office Action issued Jun. 5, 2009 in Chinese Application No. 200580004191.8 (English translation only).

Supplementary European Search Report issued Aug. 23, 2007 in European Application No. 05 70 4327.

International Search Report issued Mar. 29, 2005, International Preliminary Report on Patentability issued Sep. 19, 2006 with Written Opinion in International (PCT) Application No. PCT/JP2005/002389 (with English translation).

U.S. Office Action issued Oct. 15, 2008 in U.S. Appl. No. 10/590,111.

Chinese Office Action issued Aug. 8, 2008 in Chinese Application No. 200580005175.0 (English translation only).

International Search Report issued May 10, 2005, International Preliminary Report on Patentability issued Sep. 19, 2006 with Written Opinion in International (PCT) Application No. PCT/JP2005/002806 (with English translation).

U.S. Office Action issued Dec. 21, 2007 in U.S. Appl. No. 10/590,871.

U.S. office Action issued Aug. 22, 2008 in U.S. Appl. No. 10/590,871.

International Search Report issued Mar. 4, 2008 with Written Opinion in International (PCT) Application No. PCT/JP2008/052096 (with English translation).

C. F. Deacon, et al., "Glucagon-like peptide 1 undergoes differential tissue-specific metabolism in the anesthetized pig", American Journal of Physiology, 1996, vol. 271, pp. E458 - E464.

L.B. Knudsen, et al., "Glucagon-like peptide-1-(9-36) amide is a major metabolite of glucagon-like peptide-1-(7-36) amide after in vivo administration to dogs, and it acts as an antagonist on the pancreatic receptor", European Journal of Pharmacology, 1996, vol. 318, pp. 429-435.

E.G. Siegel, et al., "Comparison of the effect of GIP and GLP-1 (7-36amide) on insulin release from rat pancreatic islets", European Journal of Clinical Investigation, 1992, vol. 22, pp.154-157.

B. Kreymann, et al., "Glucagon-Like Peptide-1 7-36: A Physiological Incretin in Man", The Lancet, 1987, vol. 2, pp. 1300-1303.

H. Fehmann, et al., "Insulinotropic Hormone Glucagon-like Peptide-I(7-37) Stimulation of Proinsulin Gene Expression and Proinsulin Biosynthesis in Insulinoma βTC-1 Cells", Endocrinology, 1992, vol. 130, No. 1, pp. 159-166.

J. Buteau, et al., "Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells", Diabetologia, 1999, vol. 42, pp. 856-864.

J. M. Egan, et al., "Glucagon-Like Peptide-1(7-36) Amide (GLP-1) Enhances Insulin-Stimulated Glucose Metabolism in 3T3-L1 Adipocytes: One of Several Potential Extrapancreatic Sites of GLP-1 Action", Endocrinology, 1994, vol., 135 No. 1, pp. 2070-2075.

M.L. Villanueva-Peñacarrillo, et al., "Potent glycogenic effect of GLP-1(7-36)amide in rat skeletal muscle", Diabetologia, 1994, vol. 37, pp. 1163-1166.

S. Efendié, et al., "Glucagon-Like Insulinotropic Peptide Has a Stronger Antidiabetogenic Effect than Glibenclamide", Digestion, vol. 54, pp. 392-393.

M. Anvari, et al., "Effects of GLP-1 on Gastric Emptying, Antropyloric Motility, and Transpyloric Flow in Response to a Nonnutrient Liquid", Digestive Diseases and Sciences, 1998, vol. 43, No. 6, pp. 1133-1140.

J. Holst, et al , "Inhibition of the Activity of Dipeptidyl-Peptidase IV as a Treatment for Type 2 Diabetes", Diabetes, 1998, vol. 47, pp. 1663-1670.

B. Balkan, et al., "Inhibition of dipeptidyl peptidase IV with NVP-DPP728 increases plasma GLP-1 (7-36 amide) concentrations and improves oral glucose tolerance in obese Zucker rats," Diabetologia, 1999, vol. 42, pp. 1324-1331.

M. V. Blazquez, et al., "Selective Decrease of CD26 Expression in T Cells From HIV-1-Infected Individuals", The Journal of Immunology, 1992, vol. 149, No. 9, pp. 3073-3077.

M. Subramanyam, et al., "Mechanism of HIv-1 Tat Induced Inhibition of Antigen-Specific T Cell Responsiveness", The Journal of Immunology, 1993, vol. 150, No. 6, pp. 2544-2553.

E. Schön, et al., "Dipeptidyl Peptidase IV in the Immune System - Effects of Specific Enzyme Inhibitors on Activity of Dipeptidyl Peptidase IV and Proliferation of Human Lymphocytes", Biological Chemistry Hoppe-Seyler, 1991, vol. 372, pp. 305-311.

T. Mattern, et al., "Expression of CD26 (Dipeptidyl Peptidase IV) on Resting and Activated Human T-Lymphocytes", Scandinavian Journal of Immunology, 1991, vol. 33, pp. 737-748.

Schöll, et al., "Dipeptidyl Peptidase IV in Human T Lymphocytes —Impaired Induction of Interleukin 2 and Gamma Interferon Due to Specific Inhibition of Dipeptidyl Peptidase IV", Scandinavian Journal of Immunology, 1989, vol. 29, pp. 127-132.

J. Kameoka, et al., "Direct Association of Adenosine Deaminase with a T Cell Activation Antigen, CD26", Science, 1993, vol. 261, pp. 466-469.

F. Raynaud, et al., "Characterization of Specific Proteases Associated With the Surface of Human Skin Fibroblasts, and Their Modulation in Pathology", Journal of Cellular Physiology, 1992, vol. 151, pp. 378-385.

G. Vanhoof, et al., "Distribution of Proline-Specific Aminopeptidases in Human Tissues and Body Fluids", European Journal of Clinical Chemistry and Clinical Biochemistry, 1992, vol. 30, No. 6, pp. 333-338.

R. C. Johnson, et al., "Lung Endothelial Dipeptidyl Peptidase IV Is an Adhesion Molecule for Lung-metastatic Rat Breast and Prostate Carcinoma Cells", The Journal of Cell Biology, 1993, vol. 121, No. 6, pp. 1423-1432.

E. W. Della, et al., "Synthesis of Bridgehead-Bridgehead Substituted Bicycloalkanes", Australian Journal of Chemistry, 1985, vol. 38, pp. 1705-1718.

C. A. Grob, et al., "283. Die Synthese von 4-substituierten Bicyclo[2.2.2]oct-1-yl-p-nitrobenzolsulfonaten", Helvetica Chimica Acta, 1979, vol. 62, pp. 2802-2817.

S. A. Ahmed, et al., "Enamine Chemistry. Part 26. Preparation of Substituted Adamantane-2,4-diones and Bicyclo[2.2.2]octan-2-ones", Journal of Chem. Soc., Perkin I, 1979, pp. 2180-2183.

K. Morita, et al., "A Novel Cyclization of 4-Acetyl-1-methoxy-1-cyclohexene to 4-Alkoxybicyclo[2.2.2]octan-2-ones", J. Org. Chem., 1966, vol. 31, pp. 229-232.

W. Seebacher, et al., "Structural Requirements for the Antiprotozoal Activity of 4-Aminobicyclo[2.2.2]octan-2-ols", Monatshefte für Chemie, 2006, vol. 137, pp. 471-482.

J. D. Roberts, et al., "Syntheses of Some 4-Substituted Bicyclo [2.2.2]octane-1-carboxcylic Acids", J. Am. Chem. Soc., 1953, vol. 75, pp. 637-640.

International Preliminary Report on Patentability dated Sep. 9, 2008 with translation of PCT Written Opinion for PCT/JP2007/051768.

PROCESS FOR PRODUCING AMINOACETYL PYRROLIDINE CARBONITRILE DERIVATIVE AND INTERMEDIATE FOR PRODUCTION THEREOF

TECHNICAL FIELD

The present invention relates to a process for producing aminoacetyl pyrrolidine carbonitrile derivatives that act as dipeptidyl peptidase IV (DPP-IV) inhibitors and are thus useful for the prevention and treatment of type II diabetes and other DPP-IV-related diseases. The present invention also relates to intermediates for the production of aminoacetyl pyrrolidine carbonitrile derivatives.

BACKGROUND ART

Dipeptidyl peptidase IV (DPP-IV) inhibitors have recently attracted much attention as a treatment for diabetes (especially type II diabetes) and numerous derivatives have been reported as DPP-IV inhibitors. Of these derivatives, aminoacetyl pyrrolidine carbonitrile derivatives have been shown to exhibit hypoglycemic activity. Several of these compounds are reported to be promising antidiabetic agents (Non-Patent Documents 1 and 2, Patent Documents 1 through 16). The present applicant previously disclosed aminoacetyl pyrrolidine carbonitrile derivatives represented by the following structural formula (4):
(Chemical Formula 1)

Formula 4:

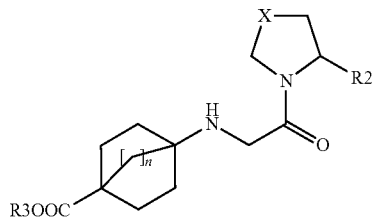

(wherein X is $CH_2$, CHF or $CF_2$; R3 is a substituted or unsubstituted $C_1$-$C_6$ alkyl group, a substituted or unsubstituted $C_3$-$C_6$ cycloalkyl group, a tetrahydropyranyl group, a substituted or unsubstituted arylmethyl group, a substituted or unsubstituted arylethyl group, a substituted or unsubstituted aromatic hydrocarbon, a substituted or unsubstituted aromatic heterocyclic ring or a substituted or unsubstituted aliphatic heterocyclic ring; and n is 1 or 2.) (Patent Document 9)

The derivatives of the formula (4) are produced by reacting a 1-(2-chloroacetyl)pyrrolidine-2-carbonitrile derivative or a 1-(2-bromoacetyl)pyrrolidine-2-carbonitrile derivative with a corresponding amine in the presence of a base (Patent Document 9). The 1-(2-chloroacetyl)pyrrolidine-2-carbonitrile derivative or the 1-(2-bromoacetyl)pyrrolidine-2-carbonitrile derivative used as the starting material is produced by reacting bromoacetyl chloride or chloroacetyl chloride with a pyrrolidine derivative (Patent Documents 1 through 9).

An alternative synthesis technique that uses neither bromoacetyl chloride nor chloroacetyl chloride is a method via a sulfonyloxyacetyl pyrrolidine derivative. Sulfonyloxyacetyl pyrrolidine derivatives are known as a general idea (Patent Documents 14 through 17). The use of 1-(2-methanesulfonyloxyacetyl)pyrrolidine-2-carbonitrile derivatives or 1-(2-toluenesulfonyloxyacetyl)pyrrolidine-2-carbonitrile derivatives is also described (Patent Documents 10 through 13). However, none of these articles specifically describes techniques for producing sulfonyloxyacetyl pyrrolidine derivatives, or the use or physical and chemical properties of these compounds, nor is it clear whether these disclosures are useful in the production of aminoacetyl pyrrolidine carbonitrile derivatives.

Non-Patent Document 1: Journal of Medicinal Chemistry, Vol. 46, p. 2774 (2003)

Non-Patent Document 2: Bioorganic & Medicinal Chemistry, Vol. 12, p. 6053 (2004)

Patent Document 1: Japanese Translation of PCT International Application No. 2000-511559

Patent Document 2: Japanese Translation of PCT International Application No. 2002-531547

Patent Document 3: Japanese Patent Application Laid-Open No. 2002-356471

Patent Document 4: Japanese Translation of PCT International Application No. 2004-500321

Patent Document 5: Japanese Translation of PCT International Application No. 2005-529078

Patent Document 6: Japanese Translation of PCT International Application No. 2004-503531

Patent Document 7: U.S. 2002/019339

Patent Document 8: WO 04/099185 Pamphlet

Patent Document 9: WO 05/075421 Pamphlet

Patent Document 10: WO 02/38541 Pamphlet

Patent Document 11: WO 03/095425 Pamphlet

Patent Document 12: Japanese Patent Application Laid-Open No. 2004-26820

Patent Document 13: Japanese Patent Application Laid-Open No. 2006-160733

Patent Document 14: Japanese Patent Application Laid-Open No. 2002-356472

Patent Document 15: Japanese Patent Application Laid-Open No. 2004-2367

Patent Document 16: Japanese Patent Application Laid-Open No. 2004-2368

Patent Document 17: WO 04/009544 Pamphlet

DISCLOSURE OF THE INVENTION

Problems to be Solved by the Invention

It is an object of the present invention to provide a safe and effective process for producing aminoacetyl pyrrolidine carbonitrile derivatives of the formula (4) that act as useful DPP-IV inhibitors. It is another object of the present invention to provide a novel intermediate for the production of aminoacetyl pyrrolidine carbonitrile derivatives.

Means for Solving the Problem

In our effort to develop processes for the production of aminoacetyl pyrrolidine carbonitrile derivatives of the formula (4), the present inventors have found that the desired compounds can be produced in a safe and effective manner by using 1-(2-sulfonyloxyacetyl)pyrrolidine-2-carboxamide derivatives and 1-(2-sulfonyloxyacetyl)pyrrolidine-2-carbonitrile derivatives as intermediates. The discovery ultimately led to the present invention.

Accordingly, the present invention comprises the following:

(1) A sulfonyloxyacetyl pyrrolidine derivative represented by the following formula:
(Chemical Formula 2)

Formula 1:

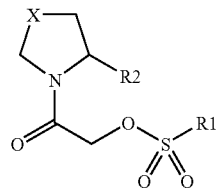

(wherein R1 is a substituted or unsubstituted $C_1$-$C_6$ alkyl group, a substituted or unsubstituted $C_3$-$C_6$ cycloalkyl group, a substituted or unsubstituted arylmethyl group, a substituted or unsubstituted aromatic hydrocarbon, a substituted or unsubstituted aromatic heterocyclic ring or a substituted or unsubstituted aliphatic heterocyclic ring; R2 is $CONH_2$ or CN; X is $CH_2$, CHF or $CF_2$.)

(2) The sulfonyloxyacetyl pyrrolidine derivative according to (1), wherein the compound represented by the formula (1) is a benzenesulfonyloxyacetyl pyrrolidine derivative represented by the following formula:
(Chemical Formula 3)

Formula 2:

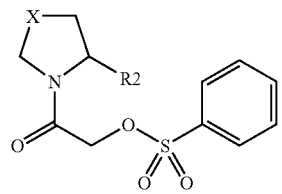

(wherein R2 and X are as defined above.)

(3) The sulfonyloxyacetyl pyrrolidine carbonitrile derivative according to (2), wherein R2 in the formula (2) is CN.

(4) The sulfonyloxyacetyl pyrrolidine carbonitrile derivative according to (3), wherein X in the formula (2) is CHF or $CF_2$.

(5) A process for producing an aminoacetyl pyrrolidine derivative represented by the following formula:
(Chemical Formula 6)

Formula 4:

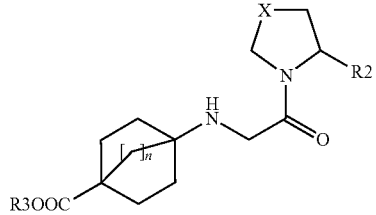

(wherein X is as defined above; R2 is $CONH_2$ or CN; R3 is a substituted or unsubstituted $C_1$-$C_6$ alkyl group, a substituted or unsubstituted $C_3$-$C_6$ cycloalkyl group, a tetrahydropyranyl group, a substituted or unsubstituted arylmethyl group, a substituted or unsubstituted arylethyl group, a substituted or unsubstituted aromatic hydrocarbon, a substituted or unsubstituted aromatic heterocyclic ring or a substituted or unsubstituted aliphatic heterocyclic ring; and n is 1 or 2), comprising the step of:

reacting a sulfonyloxyacetyl pyrrolidine derivative represented by the following formula:
(Chemical Formula 4)

Formula 1:

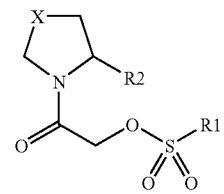

(wherein R1 is a substituted or unsubstituted $C_1$-$C_6$ alkyl group, a substituted or unsubstituted $C_3$-$C_6$ cycloalkyl group, a substituted or unsubstituted arylmethyl group, a substituted or unsubstituted aromatic hydrocarbon, a substituted or unsubstituted aromatic heterocyclic ring or a substituted or unsubstituted aliphatic heterocyclic ring; and $R_2$ and X are as defined above) with a bicycloester derivative represented by the following formula or a salt thereof:
(Chemical Formula 5)

Formula 3:

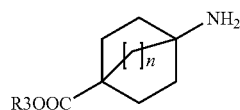

(wherein R3 and n are as defined above).

(6) A process for producing an aminoacetyl pyrrolidine derivative represented by the following formula:
(Chemical Formula 9)

Formula 4:

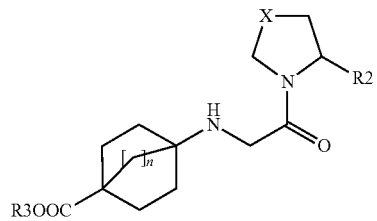

(wherein X is $CH_2$, CHF or $CF_2$; R2 is $CONH_2$ or CN; R3 is a substituted or unsubstituted $C_1$-$C_6$ alkyl group, a substituted or unsubstituted $C_3$-$C_6$ cycloalkyl group, a tetrahydropyranyl group, a substituted or unsubstituted arylmethyl group, a substituted or unsubstituted arylethyl group, a substituted or unsubstituted aromatic hydrocarbon, a substituted or unsubstituted aromatic heterocyclic ring or a substituted or unsubstituted aliphatic heterocyclic ring; and n is 1 or 2), comprising the step of:

reacting a benzenesulfonyloxyacetyl pyrrolidine derivative represented by the following formula:
(Chemical Formula 7)

Formula 2:

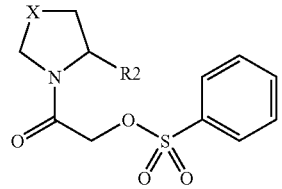

(wherein R2 and X are as defined above) with a bicycloester derivative represented by the following formula or a salt thereof:
(Chemical Formula 8)

Formula 3:

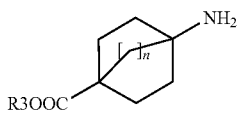

(wherein R3 and n are as defined above).

(7) A process for producing a sulfonyloxyacetyl pyrrolidine carboxamide derivative represented by the following formula:
(Chemical Formula 11)

Formula 6:

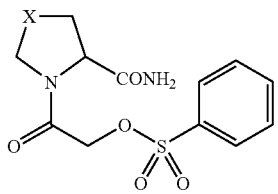

(wherein X is $CH_2$, CHF or $CF_2$), comprising the step of:
reacting a compound represented by the following formula:
(Chemical Formula 10)

Formula 5:

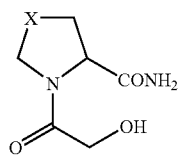

(wherein X is as defined above) with a benzenesulfonylating agent to introduce a benzenesulfonyl group into the compound to form the sulfonyloxyacetyl pyrrolidine carboxamide derivative.

(8) The process according to (7), wherein the benzenesulfonylating agent is benzenesulfonyl chloride.

(9) A process for producing the sulfonyloxyacetyl pyrrolidine carbonitrile derivative according to (4), comprising the steps of:
reacting a compound represented by the following formula:
(Chemical Formula 12)

Formula 5:

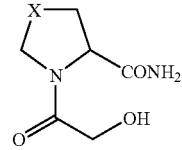

(wherein X is $CH_2$, CHF or $CF_2$) with a benzenesulfonylating agent to introduce a benzenesulfonyl group into the compound to form a sulfonyloxyacetyl pyrrolidine carboxamide derivative represented by the following formula:
(Chemical Formula 13)

Formula 6:

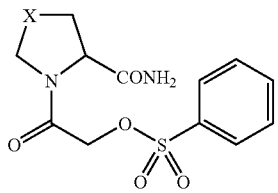

(wherein X is as defined above); and
dehydrating the sulfonyloxyacetyl pyrrolidine carboxamide derivative to form a benzensulfonyloxyacetyl pyrrolidine carbonitrile derivative represented by the following formula:
(Chemical Formula 14)

Formula 7:

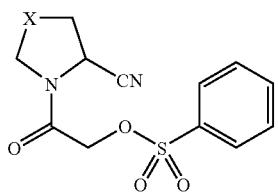

(wherein X is as defined above).

(10) The process according to (9), wherein the benzensulfonylating agent is benzenesulfonyl chloride.

Effect of the Invention

By using a 1-(2-sulfonyloxyacetyl)pyrrolidine-2-carboxamide derivative or a 1-(2-sulfonyloxyacetyl)pyrrolidine-2-carbonitrile derivative as an intermediate instead of bromoacetyl chloride or chloroacetyl chloride, each a corrosive, toxic reagent, the present inventors have established a safe, high-yield process for the production of the derivatives of the formula (4).

BEST MODE FOR CARRYING OUT THE INVENTION

As used herein, the term "substituted or unsubstituted $C_1$-$C_6$ alkyl group" refers to a $C_1$-$C_6$ alkyl group (such as methyl group, cyclopropylmethyl group, ethyl group, propyl group, 1-methylethyl group, 1-methylpropyl group, 2-methylpropyl group, 1-ethylpropyl group, 2-ethylpropyl group, butyl group, t-butyl group or hexyl group), which may have 1 to 5 substituents selected from a halogen atom, a hydroxyl group, a cyano group, a $C_1$-$C_6$ alkoxy group, a substituted or unsubstituted aryloxy group, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group that may contain 1 to 3 heteroatoms, a formylamino group, a $C_1$-$C_6$ alkylcarbonylamino group, a $C_1$-$C_6$ alkoxycarbonylamino group, a $C_1$-$C_6$ alkylsulfonylamino group, a substituted or unsubstituted arylsulfonylamino group and other substituents.

As used herein, the term "substituted or unsubstituted $C_3$-$C_6$ cycloalkyl group" refers to a $C_3$-$C_6$ cycloalkyl group (such as cyclopropyl group, cyclobutyl group, cyclopentyl group or cyclohexyl group), which may have 1 to 5 substituents selected from a halogen atom, a hydroxyl group, a cyano group, a $C_1$-$C_6$ alkoxy group, a substituted or unsubstituted aryloxy group, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a 4- to 9-membered cyclic amino group that may contain 1 to 3 heteroatoms, a formylamino group, a $C_1$-$C_6$ alkylcarbonylamino group, a $C_1$-$C_6$ alkoxycarbonylamino group, a $C_1$-$C_6$ alkylsulfonylamino group, a substituted or unsubstituted arylsulfonylamino group and other substituents.

As used herein, the term "substituted or unsubstituted arylmethyl group" refers to an arylmethyl group (such as phenylmethyl group, naphthylmethyl group, pyridylmethyl group, quinolylmethyl group or indolylmethyl group), which may have 1 to 5 substituents selected from a halogen atom, a substituted or unsubstituted $C_1$-$C_6$ alkyl group, a hydroxyl group, a cyano group, a nitro group, a substituted or unsubstituted $C_1$-$C_6$ alkoxy group, a substituted or unsubstituted aryloxy group, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a substituted or unsubstituted arylamino group, a 4- to 9-membered cyclic amino group that may contain 1 to 3 heteroatoms, a formylamino group, a $C_1$-$C_6$ alkylcarbonylamino group, a $C_1$-$C_6$ alkoxycarbonylamino group, a $C_1$-$C_6$ alkylsulfonylamino group, a substituted or unsubstituted arylsulfonylamino group and other substituents.

As used herein, the term "substituted or unsubstituted arylethyl group" refers to an arylethyl group (such as phenylethyl group, naphthylethyl group, pyridylethyl group, quinolylethyl group or indolylethyl group), which may have 1 to 5 substituents selected from a halogen atom, a substituted or unsubstituted $C_1$-$C_6$ alkyl group, a hydroxyl group, a cyano group, a nitro group, a substituted or unsubstituted $C_1$-$C_6$ alkoxy group, a substituted or unsubstituted aryloxy group, a $C_1$-$C_6$ alkylcarbonyl group, a $C_1$-$C_6$ alkoxycarbonyl group, a $C_1$-$C_6$ alkylthio group, an amino group, a mono- or di-substituted $C_1$-$C_6$ alkylamino group, a substituted or unsubstituted arylamino group, a 4- to 9-membered cyclic amino group that may contain 1 to 3 heteroatoms, a formylamino group, a $C_1$-$C_6$ alkylcarbonylamino group, a $C_1$-$C_6$ alkoxycarbonylamino group, a $C_1$-$C_6$ alkylsulfonylamino group, a substituted or unsubstituted arylsulfonylamino group and other substituents.

As used herein, the term "substituted or unsubstituted aromatic hydrocarbon" refers to an aromatic hydrocarbon (benzene ring, naphthalene ring or anthracene ring), which may have 1 to 5 substituents selected from a halogen atom, a hydroxyl group, a cyano group, a nitro group, a substituted or unsubstituted $C_1$-$C_6$ alkyl group, a $C_1$-$C_6$ alkoxy group, a $C_1$-$C_6$ alkylthio group, a $C_1$-$C_6$ dialkylamino group and other substituents.

As used herein, the term "substituted or unsubstituted aromatic heterocyclic ring" refers to an aromatic heterocyclic ring (a 5- or 6-membered aromatic monocyclic heterocyclic ring or a 9- or 10-membered aromatic fused heterocyclic ring containing 1 to 3 heteroatoms selected from a nitrogen atom, an oxygen atom and a sulfur atom. Examples include pyridine ring, pyrimidine ring, pyridazine ring, triazine ring, quinoline ring, naphthyridine ring, quinazoline ring, acridine ring, pyrrole ring, furane ring, thiophene ring, imidazole ring, pyrazole ring, oxazole ring, isoxazole ring, thiazole ring, indole ring, benzofuran ring, benzothiazole ring, benzimidazole ring and benzoxazole ring), which may have 1 to 5 substituents selected from a halogen atom, a hydroxyl group, a cyano group, a nitro group, a $C_1$-$C_6$ alkyl group, a $C_1$-$C_6$ alkoxy group, a $C_1$-$C_6$ alkylthio group and other substituents.

As used herein, the term "substituted or unsubstituted aliphatic heterocyclic ring" refers to an aliphatic heterocyclic ring (a 4- to 7-membered aliphatic monocyclic heterocyclic ring or a 9- or 10-membered aliphatic fused heterocyclic ring containing 1 to 3 heteroatoms selected from a nitrogen atom, an oxygen atom and a sulfur atom. Examples include azetidine ring, pyrrolidine ring, tetrahydrofuran ring, piperidine ring, morpholine ring and perazine ring), which may have 1 to 5 substituents selected from a halogen atom, a $C_1$-$C_6$ alkyl group, a hydroxyl group, a cyano group, a nitro group, a $C_1$-$C_6$ alkoxy group, a $C_1$-$C_6$ alkylthio group and other substituents.

While the term "salt thereof" as in "bicycloester amine derivative or a salt thereof" preferably refers to salts including hydrochlorides, hydrobromides, hydroiodides, sulfonates (such as methanesulfonates, tosylates and benzenesulfonates), carboxylates (such as acetates, trifluoroacetates, malonates, succinates and maleates), and sulfates, although the term can refer to any acceptable amine salt.

As used herein, the term "halogen atom" refers to a fluorine atom, a chlorine atom, a bromine atom or an iodine atom.

(Production Processes)

The following summarizes a process for producing an aminoacetyl pyrrolidine carbonitrile derivative of the formula (4) (where X and R3 are as defined above) via a 1-(2-benzenesulfonyloxyacetyl)pyrrolidine derivative (Scheme 1).

(Chemical Formula 15)

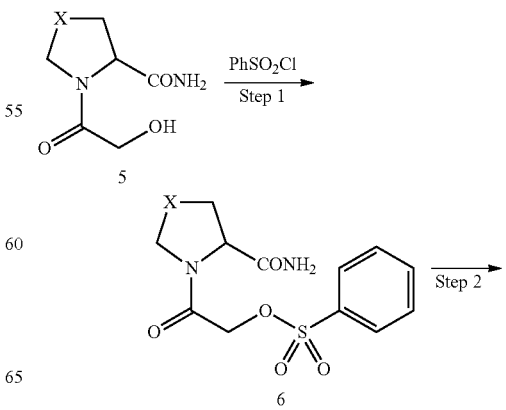

Scheme 1

-continued

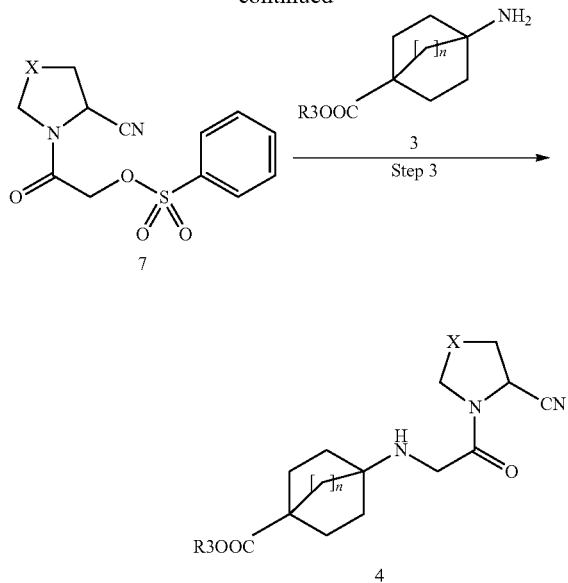

In Steps 1 and 2, a benzenesulfonyl group is introduced into a 1-(2-hydroxyacetyl)pyrrolidine carboxamide derivative of the formula (5) (where X is as defined above) to form a 1-(2-benzenesulfonyloxyacetyl)pyrrolidine carboxamide derivative of the formula (6) (where X is as defined above), which in turn is dehydrated to form a 1-(2-benzenesulfonyloxyacetyl)pyrrolidine carbonitrile derivative of the formula (7) (where X is as defined above).

The benzenesulfonylating agent used in the benzensulufonylation reaction of Step 1 is preferably benzenesulfonyl chloride or a benzenesulfonic anhydride.

When a base is used in the reaction of Step 1, it may be an alkali carbonate, such as sodium bicarbonate and potassium carbonate, or a tertiary amine, such as triethylamine, diisopropylethylamine, N-methylmorpholine, N,N,N',N'-tetramethylethylenediamine, N,N,N',N'-tetramethyl-1,3-propanediamine, diazabicyclo[5.4.0]-7-undecene, pyridine, 4-dimethylaminopyridine and 1,8-bis(dimethylamino)naphthalene. The base is preferably triethylamine, N,N,N',N'-tetramethyl-1,3-propanediamine or a mixture thereof. Trimethylamine hydrochloride may be added to the reaction mixture.

The dehydrating agent used in the dehydration reaction of Step 2 may be phosphorus pentoxide, phosphorus pentachloride, phosphorus oxychloride, thionyl chloride, oxalyl chloride, p-toluenenesulfonyl chloride, methanesulfonyl chloride, chlorosulfonyl isocyanate, N,N'-dicyclohexylcarbodiimide or trifluoroacetic anhydride. The dehydrating agent is preferably oxalyl chloride or trifluoroacetic anhydride. These dehydrating agents may be added as they are or as a solution in a proper solvent. When a base is used in the dehydration reaction, it may be an alkali carbonate, such as sodium bicarbonate and potassium carbonate, or a tertiary amine, such as triethylamine, diisopropylethylamine, N-methylmorpholine, N,N,N',N'-tetramethylethylenediamine, N,N,N',N'-tetramethyl-1,3-propanediamine, diazabicyclo[5.4.0]-7-undecene, pyridine, 4-dimethylaminopyridine and 1,8-bis(dimethylamino)naphthalene.

The solvents used in each reaction are inactive solvents that are not involved in the reaction. Examples of such solvents include tetrahydrofuran, dioxane, ethylether, dimethoxyethane, acetonitrile, ethyl acetate, toluene, xylene, dichloromethane, chloroform, 1,2-dichloroethane, N,N-dimethylformamide, N,N-dimethylacetamide, N-methyl-2-pyrrolidone and dimethylsulfoxide. Of these, tetrahydrofuran, dichloromethane and acetonitrile are preferred. Each reaction is carried out at −78° C. to 150° C., preferably at −40° C. to 25° C., and more preferably at −20° C. to −5° C.

In carrying out Steps 1 and 2, the 1-(2-benzenesulfonyloxyacetyl)pyrrolidine carboxamide derivative of the formula (6) (where X is as defined above) produced in Step 1 may not be isolated prior to Step 2.

In Step 3, the 1-(2-benzenesulfonyloxyacetyl)pyrrolidine carbonitrile derivative of the formula (7) (where X is as defined above) is reacted with an amine derivative of the formula (3) (where R3 is as defined above) in the presence or absence of a base to form an aminoacetyl pyrrolidine carbonitrile derivative of the formula (4) (where X and R3 are as defined above).

When a base is used in this reaction, it may be an alkali carbonate, such as sodium bicarbonate, potassium carbonate and cesium carbonate, or a tertiary amine, such as triethylamine, diisopropylethylamine, N-methylmorpholine, diazabicyclo[5.4.0]-7-undecene, pyridine, 4-dimethylaminopyridine, 1,8-bis(dimethylamino)naphthalene, phosphazene base and pentaisopropylguanidine. The base is preferably potassium carbonate. When a catalyst is used in the reaction, it may be a phase-transfer catalyst or an inorganic base, such as tetrabutylammonium bromide, tetrabutylammonium iodide, benzyltriethylammonium bromide, lithium bromide, lithium iodide, sodium iodide, potassium bromide, potassium iodide, cesium bromide and cesium iodide. The catalyst is preferably potassium iodide. The solvents used in the reaction are inactive solvents that are not involved in the reaction. Examples of such solvents include acetone, ethanol, tetrahydrofuran, dioxane, ethylether, dimethoxyethane, acetonitrile, ethyl acetate, toluene, xylene, dichloromethane, chloroform, 1,2-dichloroethane, N,N-dimethylformamide, N,N-dimethylacetamide, N-methyl-2-pyrrolidone and dimethylsulfoxide. Of these, N,N-dimethylformamide is preferred. The condensation reaction is carried out at −30° C. to 150° C., and preferably at 0° C. to 80° C.

Other sulfonyloxyacetyl pyrrolidine carbonitrile derivatives can also be synthesized as in Steps 1 and 2 by using corresponding sulfonylating agents. Such sulfonyloxyacetyl pyrrolidine carbonitrile derivatives can be subjected to Step 3 to produce aminoacetyl pyrrolidine carbonitrile derivatives.

Alternatively, aminoacetyl pyrrolidine carbonitrile derivatives of the formula (4) (where X and R3 are as defined above) can be produced by the following process (Scheme 2).

(Chemical Formula 16)

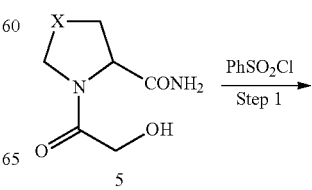

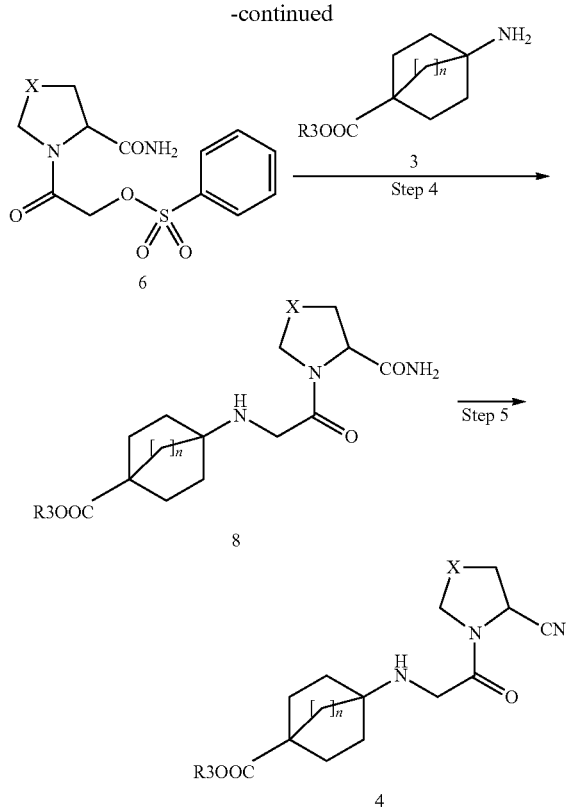

A 1-(2-benzenesulfonyloxyacetyl)pyrrolidine carboxamide derivative of the formula (6) (where X is as defined above) is first produced according to Scheme 1 (Step 1). The product is then reacted with an amine derivative of the formula (3) (where R3 is as defined above) to form an aminoacetyl pyrrolidine carboxamide derivative of the formula (8) (where X and R3 are as defined above) (Step 4), which in turn is dehydrated to form an aminoacetyl pyrrolidine carbonitrile derivative of the formula (4) (where X and R3 are as defined above) (Step 5).

Step 4 in this process can be carried out in a similar manner to Step 3, and Step 5 can be carried out in a similar manner to Step 2. Other sulfonyloxyacetyl pyrrolidine carbonitrile derivatives can also be synthesized as in Step 1 by using corresponding sulfonylating agents. Such sulfonyloxyacetyl pyrrolidine carbonitrile derivatives can be subjected to Step 4 to produce aminoacetyl pyrrolidine carboxamide derivatives of the formula (8) (where X and R3 are as defined above).

The corrosive liquid reagents, such as bromoacetyl chloride and chloroacetyl chloride, are difficult to handle and not suitable for industrial use. Furthermore, these compounds are unstable and react vigorously with water to produce hydrogen chloride and other corrosive gases. In addition, these compounds are highly toxic: they cause burns when coming into contact with the skin and cause pulmonary edema if inhaled. Since the process of the present invention uses 1-(2-benzenesulfonyloxyacetyl)pyrrolidine derivatives as reaction intermediates and thus requires neither bromoacetyl chloride nor chloroacetyl chloride, it can produce aminoacetyl pyrrolidine carbonitrile derivatives, effective DPP-IV inhibitors, in a safer manner than ever before.

Although the 1-(2-benzenesulfonyloxyacetyl)pyrrolidine carbonitrile derivatives disclosed by the present invention exhibit high reactivity with different amines, they react with bicycloester amine derivatives to give particularly high yields and are therefore particularly useful in the production of DPP-IV inhibitors in the form of bicycloester derivatives represented by the formula (4).

EXAMPLES

The present invention will now be described with reference to examples, which are not intended to limit the scope of the invention in any way. Production processes of starting materials used in Examples are also presented as Reference Examples.

Reference Example 1

Synthesis of (2S,4S)-4-fluoro-1-(2-hydroxyacetyl) pyrrolidine-2-carboxamide

Process A: Methyl (2S,4S)-4-fluoropyrrolidine-2-carboxylate hydrochloride (18.4 g) was suspended in dehydrated acetonitrile (370 mL). While the suspension was cooled in an ice bath, diisopropylethylamine (18.3 mL) was added dropwise and the mixture was stirred for 15 minutes. Subsequently, 1-hydroxybenzotriazole (4.59 g), glycolic acid (8.37 g) and 3-ethyl-1-(3-dimethylaminopropyl)carbodiimide hydrochloride (23.0 g) were added and the reaction mixture was stirred at room temperature for 6 hours and left overnight. The reaction mixture was then concentrated under reduced pressure and the resulting residue was purified on a silica gel column (eluant=ethyl acetate:methanol=10:1). The eluted yellow oil was dissolved in dehydrated methanol (50 mL). While being cooled in an ice bath, the solution was added to methanol (250 mL) saturated with ammonia. The mixture was stirred at room temperature for 3 hours. The resulting crystal was collected by filtration, washed with methanol, and dried under reduced pressure to give (2S,4S)-4-fluoro-1-(2-hydroxyacetyl)pyrrolidine-2-carboxamide as a white crystal (15.6 g, 82% yield).

Process B: Methyl (2S,4S)-4-fluoropyrrolidine-2-carboxylate hydrochloride (1.84 g) was suspended in dehydrated acetonitrile (37 mL). While the suspension was cooled in an ice bath, diisopropylethylamine (1.83 mL) was added dropwise and the mixture was stirred for 15 minutes. Subsequently, 1-hydroxybenzotriazole (0.46 g), acetoxyacetic acid (1.30 g) and 3-ethyl-1-(3-dimethylaminopropyl)carbodiimide hydrochloride (2.30 g) were added and the mixture was stirred at room temperature for 4 hours and left overnight. The reaction mixture was then concentrated under reduced pressure and the resulting residue was dissolved in ethyl acetate (150 mL). The solution was washed successively with water (20 mL), a saturated aqueous sodium bicarbonate solution (20 mL) and saturated brine (20 mL). The washes were combined and sodium chloride was added to saturation. The resulting mixture was extracted with ethyl acetate (100 mL×2). The ethyl acetate extracts were combined, dried over anhydrous sodium sulfate, and concentrated under reduced pressure. The resulting residue was dissolved in methanol (30 mL) saturated with ammonia and the solution was stirred at room temperature for 4 hours. The resulting crystal was collected by filtration, washed with methanol, and dried under reduced pressure to give (2S,4S)-4-fluoro-1-(2-hydroxyacetyl)pyrrolidine-2-carboxamide as a white crystal (1.50 g, 79% yield).

Process C: Methyl (2S,4S)-4-fluoropyrrolidine-2-carboxylate hydrochloride (1.84 g) was suspended in dehydrated acetonitrile (30 mL). While the suspension was cooled in an ice bath, triethylamine (3.10 mL) was added dropwise and the mixture was stirred for 30 minutes. To the reaction mixture, acetoxyacetyl chloride (1.13 mL) was added dropwise at the same temperature and the mixture was further stirred for 1 hour. The insoluble material in the reaction mixture was collected by filtration and washed with acetonitrile. The filtrate and the wash were combined and concentrated under reduced pressure. The resulting residue was dissolved in ethyl acetate (150 mL) and the solution was washed successively with water (20 mL) and saturated brine (2×20 mL). The washes were combined and sodium chloride was added to saturation. The resulting mixture was extracted with ethyl acetate (100 mL×2). The ethyl acetate extracts were combined, dried over anhydrous sodium sulfate, and concentrated under reduced pressure. The residue was dissolved in methanol (30 mL) saturated with ammonia and the solution was stirred at room temperature for 2.5 hours. The resulting crystal was collected by filtration, washed with methanol, and dried under reduced pressure to give (2S,4S)-4-fluoro-1-(2-hydroxyacetyl)pyrrolidine-2-carboxamide as a white crystal (1.42 g, 76% yield).

MS (CI$^+$) m/z: 191 (MH$^+$).

Elemental analysis (%): calcd for $C_7H_{11}FN_2O_3$: C, 44.21; H, 5.83; N, 14.73. found: C, 43.95; H, 5.73; N, 14.60

Reference Example 2

Synthesis of (2S)-4,4-difluoro-1-(2-hydroxyacetyl)pyrrolidine-2-carboxamide

Methyl (2S,4S)-4-fluoropyrrolidine-2-carboxylate hydrochloride (1.61 g) was suspended in dehydrated acetonitrile (25 mL). While the suspension was cooled in an ice bath, triethylamine (2.50 mL) was added dropwise and the mixture was stirred for 15 minutes. To the reaction mixture, acetoxyacetyl chloride (0.91 mL) was added dropwise at the same temperature and the mixture was further stirred for 1 hour. The insoluble material in the reaction mixture was removed by filtration and the filtrate was concentrated under reduced pressure. The residue was dissolved in ethyl acetate (150 mL) and the solution was washed successively with water (20 mL) and saturated brine (20 mL), dried over anhydrous sodium sulfate, and concentrated under reduced pressure. The resulting residue was purified on a silica gel column (eluant=ethyl acetate). The eluted pale brown tar-like material was dissolved in methanol (24 mL) saturated with ammonia and the solution was stirred at room temperature for 2 hours. The reaction mixture was then concentrated under reduced pressure and the residue was purified on a silica gel column (eluant=ethyl acetate:methanol=5:1) to give (4S)-4,4-difluoro-1-(2-hydroxyacetyl)pyrrolidine-2-carboxamide as a white resin-like material (1.66 g, 100% yield).

MS (CI$^+$) m/z: 209 (MH$^+$).

HRMS (ESI$^+$) for $C_7H_{11}F_2N_2O_3$: calcd, 209.0738; found, 209.0736.

Reference Example 3

Synthesis of (2S,4S)-4-fluoro-1-(2-hydroxyacetyl)pyrrolidine-2-carbonitrile

Step 1

Synthesis of (2S,4S)-4-fluoro-1-[2-(tert-butyldimethylsilyloxy)acetyl]pyrrolidine-2-carboxamide (2S,4S)-4-fluoro-1-(2-hydroxyacetyl)pyrrolidine-2-carboxa mide (4.10 g) and imidazole (3.27 g) were dissolved in dehydrated N,N-dimethylformamide (100 mL). While the solution was cooled in an ice bath, a solution of tert-butyldimethylsilyl chloride (3.62 g) in dehydrated N,N-dimethylformamide (30 mL) was added dropwise and the mixture was stirred at room temperature for 1 hour. The reaction mixture was then concentrated under reduced pressure and dissolved in ethyl acetate (300 mL). The ethyl acetate solution was washed successively with water (50 mL) and saturated brine (50 mL), dried over anhydrous sodium sulfate, and concentrated under reduced pressure. The resulting residue was purified on a silica gel column (eluant=ethyl acetate:methanol=10:1) to give (2S,4S)-4-fluoro-1-[2-(tert-butyldimethylsilyloxy)acetyl]pyrro lidine-2-carboxamide as a white solid (6.17 g).

MS (CI$^+$) m/z: 305 (MH$^+$).

HRMS (CI$^+$) for $C_{13}H_{26}FN_2O_3Si$: calcd, 305.1697; found, 305.1694.

Step 2

Synthesis of (2S,4S)-4-fluoro-1-[2-(tert-butyldimethylsilyloxy)acetyl]pyrro lidine-2-carbonitrile (2S,4S)-4-fluoro-1-[2-(tert-butyldimethylsilyloxy)acetyl]pyrrolidine-2-carboxamide (6.05 g) was dissolved in dehydrated tetrahydrofuran (130 mL). While the solution was cooled in an ice bath, triethylamine (9.70 mL) was added, followed by dropwise addition of trifluoroacetic anhydride (4.30 mL) and subsequent stirring at room temperature for 1 hour. The reaction mixture was then concentrated under reduced pressure and the resulting residue was dissolved in ethyl acetate (400 mL). The ethyl acetate solution was washed successively with water (50 mL), saturated aqueous sodium bicarbonate solution (50 mL) and saturated brine (50 mL), dried over anhydrous sodium sulfate, and concentrated under reduced pressure. The resulting residue was purified on a silica gel column (hexane:ethyl acetate=1:2) to give (2S,4S)-4-fluoro-1-[2-(tert-butyldimethylsilyloxy)acetyl]pyrro lidine-2-carbonitrile as a white solid (5.63 g).

MS (CI$^+$) m/z: 287 (MH$^+$).

HRMS (CI$^+$) for $C_{13}H_{24}FN_2O_2Si$: calcd, 287.1591; found, 287.1633.

Step 3

(2S,4S)-4-fluoro-1-(2-hydroxyacetyl)pyrrolidine-2-carbonitrile (2S,4S)-4-fluoro-1-[2-(tert-butyldimethylsilyloxy)acetyl]pyrrolidine-2-carbonitrile (5.50 g) was dissolved in tetrahydrofuran (37 mL). To this solution, water (37 mL) and acetic acid (115 mL) were sequentially added and the mixture was stirred at 50° C. for 7.5 hours and then at 70° C. for 9 hours. Subsequently, the reaction mixture was concentrated under reduced pressure and the resulting pale brown tar-like residue was triturated with diethyl ether. The resulting solid was collected by filtration and dried under reduced pressure to give (2S,4S)-4-fluoro-1-(2-hydroxyacetyl)pyrrolidine-2-carbonitrile as a pale brown solid (3.19 g).

MS (CI$^+$) m/z: 173 (MH$^+$).

HRMS (CI$^+$) for $C_7H_{10}FN_2O_2$: calcd, 173.0726; found, 173.0698.

Reference Example 4

Synthesis of (2S,4S)-1-[2-[(4-chlorophenyl)sulfonyloxy]acetyl]-4-fluoropyrr olidine-2-carbonitrile (2S,4S)-4-fluoro-1-(2-hydroxyacetyl)pyrrolidine-2-carboni trile (259 mg), triethylamine (0.42 mL), trimethylamine hydrochloride (143 mg) and acetonitrile (5 mL) were mixed together. While this mixture was cooled in a salt-ice bath, 4-chlorobenzenesulfonyl chloride (350 mg) was added in portions and the mixture was further stirred for 1 hour. Subsequently, water (5 mL) was added and the mixture was extracted with ethyl acetate (2×30 mL). The ethyl acetate extracts were combined, washed with saturated brine (2×5 mL), dried over anhydrous sodium sulfate, and concentrated under reduced pressure. The resulting residue was purified on a silica gel column (eluant=ethyl acetate) to give (2S,4S)-1-[2-[(4-chlorophenyl)sulfonyloxy]acetyl]-4-fluoropyrr olidine-2-carbonitrile as a white solid (256 mg, 49% yield).

MS (CI$^+$) m/z: 347 (MH$^+$).

HRMS (CI$^+$) for $C_{13}H_{13}ClFN_2O_4S$: calcd, 347.0269; found, 347.0236.

Reference Example 5

Synthesis of (2S,4S)-4-fluoro-1-[2-[(2-nitrophenyl)sulfonyloxy]acetyl]pyrro lidine-2-carbonitrile Using (2S,4S)-4-fluoro-1-(2-hydroxyacetyl)pyrrolidine-2-carbonitrile (259 mg) and 2-nitrobenzenesulfonyl chloride (366 mg), the same procedure was followed as in Reference Example 3 to give (2S,4S)-4-fluoro-1-[2-[(2-nitrophenyl)sulfonyloxy]acetyl]pyrro lidine-2-carbonitrile as a pale yellow solid (81.2 mg, 15% yield).

MS (CI$^+$) m/z: 358 (MH$^+$).
HRMS (CI$^+$) for $C_{13}H_{13}FN_3O_6S$: calcd, 358.0509; found, 358.0496.

Example 1

Synthesis of (2S,4S)-1-[2-(benzenesulfonyloxy)acetyl]-4-fluoropyrrolidine-2-carboxamide Process A: (2S,4S)-4-fluoro-1-(2-hydroxyacetyl)pyrrolidine-2-carboxamide (381 mg) and trimethylamine hydrochloride (191 mg) were suspended in acetonitrile (10 mL) and triethylamine (0.56 mL) was added to the suspension. While this mixture was cooled in a salt-ice bath, benzenesulfonyl chloride (0.28 mL) was added drop wise. The mixture was stirred for 1 hour at the same temperature, after which water (5 mL) was added and the mixture was extracted with ethyl acetate (2×40 mL). The ethyl acetate extracts were combined, dried over anhydrous sodium sulfate, and concentrated under reduced pressure. The resulting residue was purified on a silica gel column (eluant=ethyl acetate:methanol=10:1) to give (2S,4S)-1-[2-(benzenesulfonyloxy)acetyl]-4-fluoropyrrolidine-2-carboxamide as a white solid (528 mg, 80% yield).

Process B:
(2S,4S)-4-fluoro-1-(2-hydroxyacetyl)pyrrolidine-2-carboxamide (381 mg) was suspended in acetonitrile (10 mL). To this suspension, N,N,N',N'-tetramethyl-1,3-propanediamine (34.0 μL) and triethylamine (0.56 mL) were added. While the mixture was cooled in a salt-ice bath, benzenesulfonyl chloride (0.28 mL) was added dropwise. The mixture was then stirred at the same temperature for 1 hour, followed by the addition of saturated brine (5 mL) and extraction with ethyl acetate (2×40 mL). The ethyl acetate extracts were combined, dried over anhydrous sodium sulfate, and concentrated under reduced pressure. The resulting residue was purified on a silica gel column (eluant=ethyl acetate:methanol=10:1) to give (2S,4S)-1-[2-(benzenesulfonyloxy)acetyl]-4-fluoropyrrolidine-2-carboxamide as a white solid (599 mg, 91% yield).

Process C:
(2S,4S)-4-fluoro-1-(2-hydroxyacetyl)pyrrolidine-2-carboxamide (100 mg) and triethylamine (74 mg) were suspended in acetonitrile (1 mL). While the suspension was cooled in an ice bath, benzenesulfonic anhydride (188 mg) was added and the mixture was stirred for 10 minutes. Subsequently, the mixture was stirred at room temperature for 1 hour, followed by the addition of water (2 mL) and extraction with ethyl acetate (2×4 mL). The organic layers were combined, dried over anhydrous sodium sulfate, and concentrated under reduced pressure to give (2S,4S)-1-[2-(benzenesulfonyloxy)acetyl]-4-fluoropyrrolidine-2-carboxamide as a brown oil (147 mg, 85% yield).

MS (ESI$^+$) m/z: 331 (MH$^+$).
HRMS (ESI$^+$) for $C_{13}H_{16}FN_2O_5S$: calcd, 331.07639; found, 331.07953.

Example 2

Synthesis of (2S)-1-[2-(benzenesulfonyloxy)acetyl]-4,4-difluoropyrrolidine-2-carboxamide (2S)-4,4-difluoro-1-(2-hydroxyacetyl)pyrrolidine-2-carboxamide (1.66 g) was suspended in acetonitrile (40 mL). To this suspension, N,N,N',N'-tetramethyl-1,3-propanediamine (133 μL) and triethylamine (2.20 mL) were added. While the mixture was cooled in a salt-ice bath, benzenesulfonyl chloride (1.20 mL) was added dropwise. The reaction mixture was then stirred at the same temperature for 1 hour, followed by the addition of saturated brine (20 mL) and extraction with ethyl acetate (2×80 mL). The ethyl acetate extracts were combined, dried over anhydrous sodium sulfate, and concentrated under reduced pressure. To the resulting residue, a mixture of ethyl acetate and methanol (20:1, 30 mL) was added and the resulting crystal was collected by filtration to give (2S)-1-[2-(benzenesulfonyloxy)acetyl]-4,4-difluoropyrrolidine-2-carboxamide as a white crystal (1.60 g). The filtrate was concentrated under reduced pressure and the residue was purified on a silica gel column (ethyl acetate:methanol=20:1) to give additional (2S)-1-[2-(benzenesulfonyloxy)acetyl]-4,4-difluoropyrrolidine-2-carboxamide (0.58 g). The total amount of the product was 2.18 g (79% yield).

MS (CI$^+$) m/z: 349 (MH$^+$).
HRMS (ESI$^+$) for $C_{13}H_{15}F_2N_2O_5S$: calcd, 349.0670; found, 349.0665.

Example 3

Synthesis of (2S,4S)-1-[2-(benzenesulfonyloxy)acetyl]-4-fluoropyrrolidine-2-carbonitrile (Synthesis process 1)

(2S,4S)-1-[2-(benzenesulfonyloxy)acetyl]-4-fluoropyrrolid ine-2-carboxamide (516 mg) was dissolved in acetonitrile (10 mL) and triethylamine (0.52 mL) was added to the solution. While this mixture was cooled in an ice bath, trifluoroacetic anhydride (0.27 mL) was added dropwise and the mixture was stirred at room temperature for 1 hour. Subsequently, the reaction mixture was concentrated under reduced pressure. Water (5 mL) was added to the residue and the resulting crystal was collected by filtration. The filtered solid was washed with water and was dried under reduced pressure to give (2S,4S)-1-[2-(benzenesulfonyloxy)acetyl]-4-fluoropyrrolidine-2-carbonitrile as a white crystal (339 mg, 70% yield).

MS (CI$^+$) m/z: 313 (MH$^+$).
HRMS (CI$^+$) for $C_{13}H_{14}FN_2O_4S$: calcd, 313.0658; found, 313.0628.

Example 4

Synthesis of (2S,4S)-1-[2-(benzenesulfonyloxy)acetyl]-4-fluoropyrrolidine-2-carbonitrile (Synthesis process 2)

(2S,4S)-4-fluoro-1-(2-hydroxyacetyl)pyrrolidine-2-carboxa mide (381 mg) and trimethylamine hydrochloride (191 mg) were suspended in acetonitrile (10 mL) and triethylamine (1.20 mL) was added to the suspension. While this mixture was cooled in a salt-ice bath, benzenesulfonyl chloride (0.28 mL) was added dropwise. The mixture was stirred at the same temperature for 1 hour and trifluoroacetic anhydride (0.34 mL) was added dropwise. The mixture was further stirred for 1 hour. Subsequently, water (10 mL) was added to the reaction mixture and acetonitrile was evaporated under reduced pressure. The resulting crystal was collected by filtration, resuspended in diethylether (10 mL) and collected again by filtration. The collected crystal was dried under reduced pressure to give (2S,4S)-1-[2-(benzenesulfonyloxy) acetyl]-4-fluoropyrrolidine-2-carbonitrile as a white crystal (472 mg, 75% yield). This compound was identical to the compound obtained in Example 3.

Example 5

(2S,4S)-1-[2-(benzenesulfonyloxy)acetyl]-4-fluoro-pyrrolidine-2-carbonitrile (Synthesis process 3)

(2S,4S)-4-fluoro-1-(2-hydroxyacetyl)pyrrolidine-2-carboxa mide (381 mg) was suspended in acetonitrile and N,N,N',N'-tetramethyl-1,3-propanediamine (34.0 µL) and triethylamine (0.98 mL) were added to the suspension. While this mixture was cooled in a salt-ice bath, benzenesulfonyl chloride (0.28 mL) was added dropwise. The mixture was stirred at the same temperature for 1 hour and trifluoroacetic anhydride (0.34 mL) was added dropwise, followed by stirring for another 1 hour. Subsequently, water (10 mL) was added to the reaction mixture and acetonitrile was evaporated under reduced pressure. The resulting crystal was collected by filtration, washed successively with water and diethyl ether, and dried under reduced pressure to give (2S,4S)-1-[2-(benzenesulfonyloxy)acetyl]-4-fluoropyrrolidine-2-carbonitrile as a white crystal (567 mg, 91% yield). This compound was identical to the compound obtained in Example 3.

Example 6

Synthesis of (2S)-1-[2-(benzenesulfonyloxy)acetyl]-4,4-difluoropyrrolidine-2-carbonitrile (2S)-1-[2-(benzenesulfonyloxy)acetyl]-4,4-difluoropyrroli dine-2-carboxamide (872 mg) was dissolved in acetonitrile (16 mL), followed by triethylamine (1.05 mL). While this mixture was cooled in a salt-ice bath, trifluoroacetic anhydride (0.53 mL) was added dropwise. The mixture was stirred at the same temperature for 1 hour, followed by the addition of water (16 mL) and extraction with ethyl acetate (2×60 mL). The ethyl acetate extracts were combined, washed with saturated brine (2×20 mL), dried over anhydrous sodium sulfate, and concentrated under reduced pressure. The resulting residue was purified on a silica gel column (eluant=hexane:ethyl acetate=1:1) to give (2S)-1-[2-(benzenesulfonyloxy)acetyl]-4,4-difluoropyrrolidine-2-carbonitrile as a white crystal (789 mg, 96% yield).

MS (CI$^+$) m/z: 331 (MH$^+$).

HRMS (CI$^+$) for $C_{13}H_{13}F_2N_2O_4S$: calcd, 331.0564; found, 331.0558.

Example 7

Synthesis of (2S,4S)-1-[2-[(4-ethoxycarbonylbicyclo [2.2.2]oct-1-yl)amino]ac etyl]-4-fluoropyrrolidine-2-carbonitrile (Synthesis process 1)

Ethyl 4-aminobicyclo[2.2.2]octane-1-carboxylate hydrochloride (206 mg), potassium carbonate (243.2 mg), potassium iodide (13.3 mg) and N,N-dimethylformamide (5 mL) were mixed together. To this mixture, a solution of (2S,4S)-4-fluoro-1-[2-(benzenesulfonyloxy)acetyl]pyrrolidine-2-carbonitrile (250 mg) in N,N-dimethylformamide (1.5 mL) was added at 50° C. and the mixture was further stirred for 1 hour. Subsequently, the reaction mixture was concentrated under reduced pressure and the residue was purified on a silica gel column (eluant=ethyl acetate:methanol=20:1) to give (2S,4S)-1-[2-[(4-ethoxycarbonylbicyclo[2.2.2]oct-1-yl) amino]ac etyl]-4-fluoropyrrolidine-2-carbonitrile as a white solid (260 mg, 92% yield).

MS (ESI$^+$) m/z: 352 (MH$^+$)

HRMS (ESI$^+$) for $C_{18}H_{27}FN_3O_3$: calcd, 352.20364; found, 352.20256.

Example 8

Synthesis of (2S,4S)-1-[2-[(4-ethoxycarbonylbicyclo [2.2.2]oct-1-yl)amino]ac etyl]-4-fluoropyrrolidine-2-carbonitrile (Synthesis process 2)

Ethyl 4-aminobicyclo[2.2.2]octane-1-carboxylate hydrobromide (612 mg), potassium carbonate (608 mg) and N,N-dimethylformamide (4 mL) were mixed together. To this mixture, (2S,4S)-4-fluoro-1-[2-(benzenesulfonyloxy)acetyl] pyrrolidine-2-carbonitrile (625 mg) was added at 40° C. and the mixture was further stirred for 1 hour. Subsequently, water (10 mL) was added and the resulting crystal was collected by filtration. This product was washed with water (5 mL) and dried at 50° C. under reduced pressure to give (2S,4S)-1-[2-[(4-ethoxycarbonylbicyclo[2.2.2]oct-1-yl)amino]ac etyl]-4-fluoropyrrolidine-2-carbonitrile as a colorless powder (581 mg, 83% yield). This compound was identical to the compound obtained in Example 7.

Example 9

Synthesis of (2S,4S)-1-[2-[(4-ethoxycarbonylbicyclo [2.2.2]oct-1-yl)amino]ac etyl]-4-fluoropyrrolidine-2-carbonitrile (Synthesis process 3)

Using ethyl 4-aminobicyclo[2.2.2]octane-1-carboxylate benzenesulfonate (609 mg) and (2S,4S)-4-fluoro-1-[2-(benzenesulfonyloxy)acetyl]pyrrolidine-2-carbonitrile (783 mg), the same procedure was followed as in Example 7 to give (2S,4S)-1-[2-[(4-ethoxycarbonylbicyclo[2.2.2]oct-1-yl) amino]ac etyl]-4-fluoropyrrolidine-2-carbonitrile (609 mg, 87% yield). This compound was identical to the compound obtained in Example 7.

Example 10

Synthesis of (2S,4S)-1-[2-[(4-ethoxycarbonylbicyclo [2.2.2]oct-1-yl)amino]ac etyl]-4-fluoropyrrolidine-2-carbonitrile (Synthesis process 4)

Using ethyl 4-aminobicyclo[2.2.2]octane-1-carboxylate trifluoroacetate (685 mg), (2S,4S)-4-fluoro-1-[2-(benzenesulfonyloxy)acetyl]pyrrolidine-2-carbonitrile (625 mg) and potassium iodide (33.2 mg), the same procedure was followed as in Example 7 to give (2S,4S)-1-[2-[(4-ethoxycarbonylbicyclo[2.2.2]oct-1-yl)amino]ac etyl]-4-fluoropyrrolidine-2-carbonitrile (511 mg, 73% yield). This compound was identical to the compound obtained in Example 7.

Example 11

Synthesis of (2S,4S)-1-[2-[(4-ethoxycarbonylbicyclo[2.2.2]oct-1-yl)amino]ac etyl]-4-fluoropyrrolidine-2-carbonitrile (Synthesis process 5)

Using ethyl 4-aminobicyclo[2.2.2]octane-1-carboxylate methanesulfonate (645 mg), (2S,4S)-4-fluoro-1-[2-(benzenesulfonyloxy)acetyl]pyrrolidine-2-carbonitrile (625 mg) and potassium iodide (33.2 mg), the same procedure was followed as in Example 7 to give (2S,4S)-1-[2-[(4-ethoxycarbonylbicyclo[2.2.2]oct-1-yl)amino]ac etyl]-4-fluoropyrrolidine-2-carbonitrile (553 mg, 79% yield). This compound was identical to the compound obtained in Example 7.

Example 12

Synthesis of (2S)-1-[2-[(4-ethoxycarbonylbicyclo[2.2.2]oct-1-yl)amino]acety l]-4,4-difluoropyrrolidine-2-carbonitrile Ethyl 4-aminobicyclo[2.2.2]octane-1-carboxylate hydrochloride (232 mg), potassium carbonate (274 mg), potassium iodide (15.0 mg) and N,N-dimethylformamide (6 mL) were mixed together. To this mixture, a solution of (2S)-1-[2-(benzenesulfonyloxy)acetyl]pyrrolidine-4,4-difluoro-2-carbonitrile (297 mg) in N,N-dimethylformamide (2 mL) was added at 50° C. and the mixture was further stirred for 1 hour. Subsequently, the reaction mixture was concentrated under reduced pressure and the residue was purified on a silica gel column (eluant=ethyl acetate:hexane=2:1) to give (2S)-1-[2-[(4-ethoxycarbonylbicyclo[2.2.2]oct-1-yl)amino]acety l]-4,4-difluoropyrrolidine-2-carbonitrile as a white crystal (301 mg, 91% yield).

MS (ESI$^+$) m/z: 370 (MH$^+$).

HRMS (ESI$^+$) for $C_{18}H_{26}F_2N_3O_3$: calcd, 370.19422; found, 370.19348.

Example 13

Synthesis of (2S,4S)-1-[2-[(4-ethoxycarbonylbicyclo[2.2.2]oct-1-yl)amino]ac etyl]-4-fluoropyrrolidine-2-carboxamide Ethyl 4-aminobicyclo[2.2.2]octane-1-carboxylate hydrochloride (4.63 g), potassium carbonate (5.47 g) and N,N-dimethylformamide (40 mL) were mixed together. To this mixture, a solution of (2S,4S)-1-[2-(benzenesulfonyloxy)acetyl]-4-fluoropyrrolidine-2-carboxamide (5.93 g) in N,N-dimethylformamide (10 mL) was added at 40° C. and the mixture was stirred at 45° C. for 3 hours. Subsequently, the reaction mixture was concentrated under reduced pressure. Water (50 mL) was then added to the residue and the resulting crystal was collected by filtration, washed with water (30 mL), and dried at 50° C. under reduced pressure. The crude crystal was recrystallized from ethyl acetate (40 mL), washed with ethyl acetate (20 mL), and dried at room temperature under reduced pressure. This gave (2S,4S)-1-[2-[(4-ethoxycarbonylbicyclo[2.2.2]oct-1-yl)amino]ac etyl]-4-fluoropyrrolidine-2-carboxamide as a white solid in the form of colorless powder (1.81 g). The filtrate and the wash were combined and concentrated to 20 mL. The resulting crystal was collected by filtration, washed with a mixture of ethyl acetate and diisopropyl ether (1:1, 20 mL) to give additional 1.19 g of the product. The total amount of the product was 3.00 g (45% yield).

MS (ESI$^+$) m/z: 370 (MH$^+$).

Example 14

Synthesis of (2S,4S)-1-[2-[(4-ethoxycarbonylbicyclo[2.2.2]oct-1-yl)amino]ac etyl]-4-fluoropyrrolidine-2-carbonitrile (Synthesis process 6)

Trifluoroacetic anhydride (80 µL) was added to a solution of (2S,4S)-1-[2-[(4-ethoxycarbonylbicyclo[2.2.2]oct-1-yl)amino]ac etyl]-4-fluoropyrrolidine-2-carboxamide (100 mg) in tetrahydrofuran (1 mL). The mixture was stirred at room temperature for 2 hours and then at 40° C. for 1.5 hours. Subsequently, additional trifluoroacetic anhydride (40 µL) was added and the mixture was further stirred for 30 minutes. A saturated aqueous sodium bicarbonate solution (5 mL) was then added and the reaction mixture was extracted with ethyl acetate (2×10 mL). The ethyl acetate extracts were combined, washed with saturated brine (5 mL), dried over anhydrous sodium sulfate, and concentrated under reduced pressure. The resulting residue was purified on an aminated silica gel column (eluant=ethyl acetate:methanol=30:1) to give (2S,4S)-1-[2-[(4-ethoxycarbonylbicyclo[2.2.2]oct-1-yl)amino] ac etyl]-4-fluoropyrrolidine-2-carbonitrile as a colorless solid (63.7 mg, 67% yield). This compound was identical to the compound obtained in Example 7.

Comparative Examples (1) Advantageous Effects in the Production of Aminoacetyl Pyrrolidine Derivatives We now discuss the usefulness of 1-(2-benzenesulfonyloxyacetyl)pyrrolidine carbonitrile derivatives in the production (Step 3 in the above-described Scheme) of aminoacetyl-cyano pyrrolidine derivatives of the formula (4). According to the production process described in Patent Document 9, a 1-(2-chloroacetyl)pyrrolidine-2-carbonitrile derivative or a 1-(2-bromoacetyl)pyrrolidine-2-carbonitrile derivative is reacted with a corresponding amine. This process produces trialkylated by-products, resulting in a decreased yield of the desired product and a reduced purification efficiency. The ratios of trialkylated forms in the reaction products are shown in Table 1 for 1-(2-bromoacetyl)pyrrolidine-2-carbonitrile derivative (Comparative Example 1), 1-(2-chloroacetyl)pyrrolidine-2-carbonitrile derivative (Comparative Example 2) and 1-(2-benzenesulfonyloxyacetyl)pyrrolidine carbonitrile derivative (Reference Example 6). In each of Reference Example 6 and Comparative Examples 1 and 2, the ratio of the trialkylated form was determined as follows: each test compound (2.00 mmol) was added to a suspension of ethyl 4-aminobicyclo[2.2.2]octane-1-carboxylate (514 mg, 2.20 mmol) and potassium carbonate (608 mg, 4.40 mmol) in N,N-dimethylformamide (4 mL). The mixture was stirred in a heat bath at 30° C. and the reaction was monitored by HPLC. Once the disappearance of the test compound was confirmed, the reaction mixture was concentrated under reduced pressure and the ratio of the peak intensity of the trialkylated form to that of the dialkylated form in the reaction product was measured in HPLC. Since the UV absorption intensity of each trialkylated form is higher than the corresponding dialkylated form (weight ratio), the measurements were corrected by multiplying the peak intensity of each trialkylated form by a correction factor of 0.577.

TABLE 1

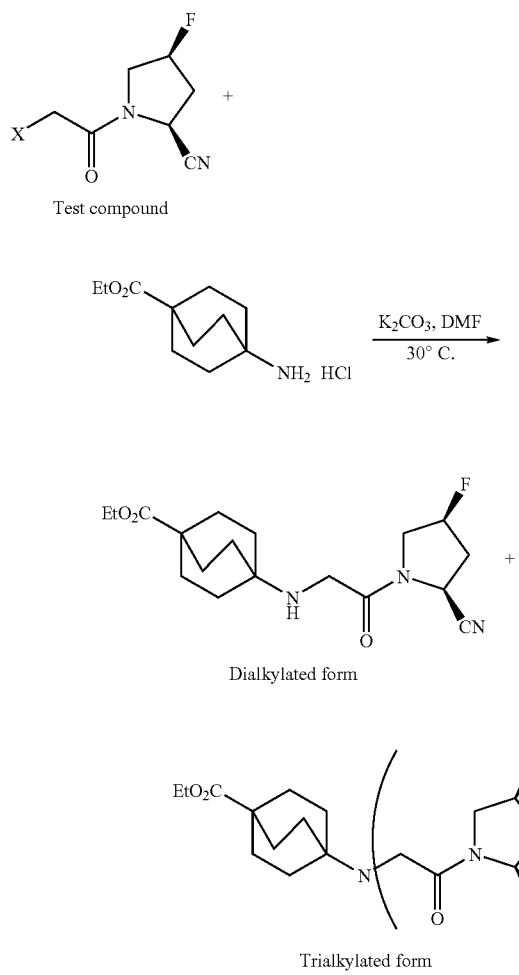

Test compound

Dialkylated form

Trialkylated form

TABLE 1-continued

| Test compound | | Reaction time (h) | Dialkylated form:Trialkylated form Corrected ratio (by weight) |
|---|---|---|---|
| Reference Example 6 | X = OSO$_2$Ph | 4 | 189:1 |
| Comparative Example 1 | X = Br | 4 | 19:1 |
| Comparative Example 2 | X = Cl | 30 | 78:1 |

\* Conditions for HPLC
Detector: UV absorptiometer (measurement wavelength: 205 nm)
Column: Inertsil ODS-3 (trade name, GL science Inc.) 4.6 mm (ID) × 15 cm (L)
Guard column: Inertsil ODS-3 (trade name, GL science Inc.) 4.0 mm (ID) × 10 cm (L)
Column temperature: 30° C.
Mobile phase: Solution A = 0.1% aqueous phosphoric acid containing 5 mmol/L sodium 1-octanesulfonate; Solution B = acetonitrile for LC. Solution A: Solution B = 73:27
Flow rate = 1.0 mL/min The results in Table 1 demonstrate that the use of the compound of the present invention results in a significantly less amount of trialkylated by-product produced as compared to each of the compounds of Comparative Examples. The same results are observed when 1-(2-benzenesulfonyloxyacetyl)pyrrolidine carboxamide derivatives were used.

(2) Advantageous Effects in the Production of Sulfonyloxyacetyl Pyrrolidine Derivatives Efficiency of the production process was significantly increased by using benzenesulfonyloxyacetyl pyrrolidine carboxamide derivatives.

We used different sulfonyloxy groups in the production of sulfonyloxyacetyl pyrrolidine carboxamides and observed differences. Table 2 shows the yields of a methanesulfonyloxy derivative and a toluenesulfonyloxy derivative described in Patent Documents 10 through 13, along with the yield of a benzenesulfonyloxy derivative disclosed by the present invention. Comparative Examples 3 and 4 were carried out using the same conditions as in Example 1, except that methanesulfonyl chloride and toluenesulfonyl chloride were used instead of benzenesulfonyl chloride.

TABLE 2

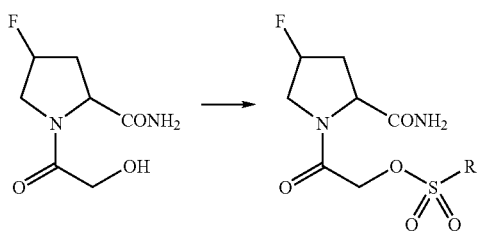

| | | | Conditions | | |
|---|---|---|---|---|---|
| | Reagents | Solvent | Reaction temperature | R | Yields (%) |
| Example 1 | Benzenesulfonyl chloride | Acetonitrile | −15° C. | C$_6$H$_5$ | 80 |
| Comparative Example 3 | Methanesulfonyl chloride | Acetonitrile | −15° C. | CH$_3$ | — |
| Comparative Example 4 | Toluenesulfonyl chloride | Acetonitrile | −15° C. | 4-CH$_3$—C$_6$H$_4$ | 48 |

When methanesulfonyl chloride was used as the sulfonyloxy-introducing agent (Comparative Example 3), the desired compound was hardly isolated. The yield was low when toluenesulfonyl chloride was used as the sulfonyloxy-introducing agent (Comparative Example 4). The use of benzenesulfonyl chloride significantly improved the efficiency of sulfonylation (Example 1).

When a commercially available proline ester derivative is used to synthesize a sulfonyloxyacetyl pyrrolidine carbonitrile derivative, the number of steps involved can be minimized and the efficiency of the process can be improved by carrying out the process so that it proceeds via a sulfonyloxyacetyl pyrrolidine carboxamide and the conversion to nitrile group is carried out during the final step. When methanesulfonyl chloride (Comparative Example 3) or toluenesulfonyl chloride (Comparative Example 4) was used, the yield of the corresponding carbonitrile derivative decreased consequently. In comparison, the efficiency of sulfonylation was improved by the use of benzenesulfonyl chloride (Example 1), as was the yield of the corresponding 1-(2-benzenesulfonyloxyacetyl)pyrrolidine carbonitrile derivative. The yield was improved even more when the 1-(2-benzenesulfonyloxyacetyl)pyrrolidine carboxamide derivative was not isolated prior to the subsequent dehydration step (Examples 4 and 5). These results indicate that the process of the present invention is particularly efficient when benzenesulfonyloxyacetyl pyrrolidine carbonitrile derivatives are used.

INDUSTRIAL APPLICABILITY

The present invention relates to benzenesulfonyloxy pyrrolidine derivatives, novel intermediates for the production of aminoacetylcyano pyrrolidine derivatives of the formula (4), as well as to a production method thereof. The process of the present invention does not require chloroacetyl chloride and so on and thus ensures the safe and efficient production of aminoacetylcyano pyrrolidine derivatives of the formula (4). The present invention, therefore, is of significant industrial importance.

The invention claimed is:

1. A sulfonyloxyacetyl pyrrolidine derivative represented by the following formula:

Formula 1:

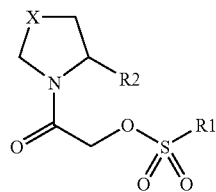

(wherein R1 is a substituted or unsubstituted $C_1$-$C_6$ alkyl group, a substituted or unsubstituted $C_3$-$C_6$ cycloalkyl group, a substituted or unsubstituted arylmethyl group, a substituted or unsubstituted aromatic hydrocarbon, a substituted or unsubstituted aromatic heterocyclic ring or a substituted or unsubstituted aliphatic heterocyclic ring; R2 is $CONH_2$ or CN; X is $CH_2$, CHF or $CF_2$).

2. The sulfonyloxyacetyl pyrrolidine derivative according to claim 1, wherein the compound represented by the formula (1) is a benzenesulfonyloxyacetyl pyrrolidine derivative represented by the following formula:

Formula 2:

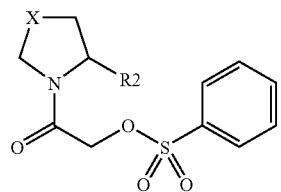

(wherein R2 and X are as defined above).

3. The sulfonyloxyacetyl pyrrolidine derivative according to claim 2, wherein R2 in the formula (2) is CN.

4. The sulfonyloxyacetyl pyrrolidine derivative according to claim 3, wherein X in the formula (2) is CHF or $CF_2$.

5. A process for producing an aminoacetyl pyrrolidine derivative represented by the following formula:

Formula 4:

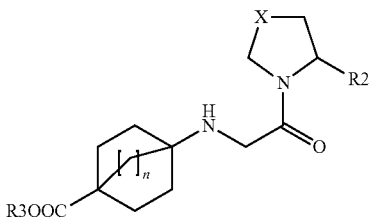

(wherein X is $CH_2$, CHF or $CF_2$; R2 is $CONH_2$ or CN; R3 is a substituted or unsubstituted $C_1$-$C_6$ alkyl group, a substituted or unsubstituted $C_3$-$C_6$ cycloalkyl group, a tetrahydropyranyl group, a substituted or unsubstituted arylmethyl group, a substituted or unsubstituted arylethyl group, a substituted or unsubstituted aromatic hydrocarbon, a substituted or unsubstituted aromatic heterocyclic ring or a substituted or unsubstituted aliphatic heterocyclic ring; and n is 1 or 2), comprising the step of:

reacting a sulfonyloxyacetyl pyrrolidine derivative represented by the following formula:

Formula 1:

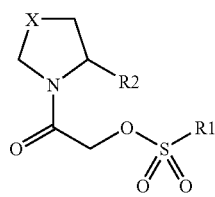

(wherein R1 is a substituted or unsubstituted $C_1$-$C_6$ alkyl group, a substituted or unsubstituted $C_3$-$C_6$ cycloalkyl group, a substituted or unsubstituted arylmethyl group, a substituted or unsubstituted aromatic hydrocarbon, a substituted or unsubstituted aromatic heterocyclic ring or a substituted or unsubstituted aliphatic heterocyclic ring; and $R_2$ and X are as defined above) with a bicycloester derivative represented by the following formula or a salt thereof:

Formula 3:

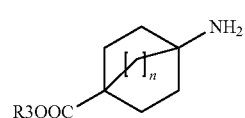

(wherein R3 and n are as defined above).

6. A process for producing an aminoacetyl pyrrolidine derivative represented by the following formula:

Formula 4:

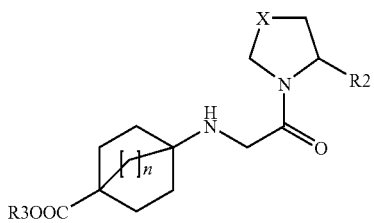

(wherein X is CH$_2$, CHF or CF$_2$; R2 is CONH$_2$ or CN; R3 is a substituted or unsubstituted C$_1$-C$_6$ alkyl group, a substituted or unsubstituted C$_3$-C$_6$ cycloalkyl group, a tetrahydropyranyl group, a substituted or unsubstituted arylmethyl group, a substituted or unsubstituted arylethyl group, a substituted or unsubstituted aromatic hydrocarbon, a substituted or unsubstituted aromatic heterocyclic ring or a substituted or unsubstituted aliphatic heterocyclic ring; and n is 1 or 2), comprising the step of:
reacting a benzenesulfonyloxyacetyl pyrrolidine derivative represented by the following formula:

Formula 2:

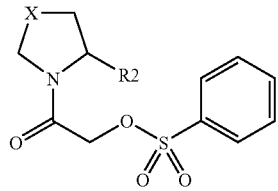

(wherein R2 and X are as defined above) with a bicycloester derivative represented by the following formula or a salt thereof:

Formula 3:

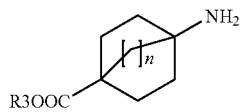

(wherein R3 and n are as defined above).

7. A process for producing a sulfonyloxyacetyl pyrrolidine carboxamide derivative represented by the following formula:

Formula 6:

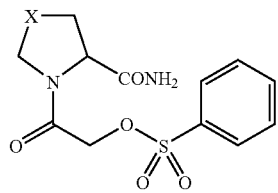

(wherein X is CH$_2$, CHF or CF$_2$), comprising the step of:
reacting a compound represented by the following formula:

Formula 5:

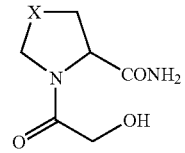

(wherein X is as defined above) with a benzenesulfonylating agent to introduce a benzenesulfonyl group into the compound to form the sulfonyloxyacetyl pyrrolidine carboxamide derivative.

8. The process according to claim 7, wherein the benzenesulfonylating agent is benzenesulfonyl chloride.

9. A process for producing the sulfonyloxyacetyl pyrrolidine derivative according to claim 4, comprising the steps of:
reacting a compound represented by the following formula:

Formula 5:

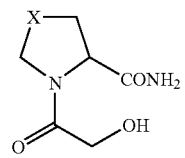

(wherein X is CH$_2$, CHF or CF$_2$) with a benzenesulfonylating agent to introduce a benzenesulfonyl group into the compound to form a sulfonyloxyacetyl pyrrolidine carboxamide derivative represented by the following formula:

Formula 6:

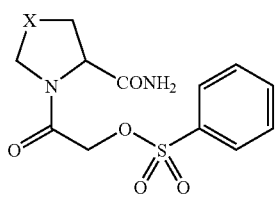

(wherein X is as defined above); and
dehydrating the sulfonyloxyacetyl pyrrolidine carboxamide derivative to form a benzensulfonyloxyacetyl pyrrolidine carbonitrile derivative represented by the following formula:

Formula 7:

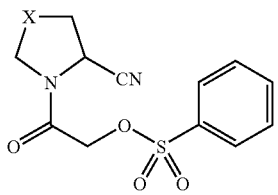

(wherein X is as defined above).

* * * * *